United States Patent

Hanzawa et al.

[11] Patent Number: 5,932,744
[45] Date of Patent: Aug. 3, 1999

[54] PROCESS FOR THE PREPARATION OF CIS-HEXAHYDROISOINDOLINE DERIVATIVES

[75] Inventors: Yasushi Hanzawa; Masahiro Kusano; Hitoshi Koike, all of Tokyo, Japan

[73] Assignee: Yuki Gosei Kogyo Co., Ltd., Tokyo, Japan

[21] Appl. No.: 09/128,465

[22] Filed: Aug. 4, 1998

[30] Foreign Application Priority Data

Aug. 28, 1997 [JP] Japan .................................. 9-247631

[51] Int. Cl.$^6$ ................................................ C07D 209/44
[52] U.S. Cl. .......................................................... 548/515
[58] Field of Search ............................................. 548/515

[56] References Cited

U.S. PATENT DOCUMENTS

| | | | |
|---|---|---|---|
| 5,202,335 | 4/1993 | Sato et al. ........................... | 548/515 X |
| 5,409,929 | 4/1995 | Ciganek ............................... | 548/515 X |

FOREIGN PATENT DOCUMENTS 44-005219  3/1969  Japan ...................................... 548/515

OTHER PUBLICATIONS

Dunet et al., Bull. Chem. Soc. France, 1956, 906–910.

Primary Examiner—Fiona T. Powers
Attorney, Agent, or Firm—Gary M. Nath; Nath & Associates

[57] ABSTRACT

The instant invention provides a process for the industrial preparation of cis-hexahydroisoindoline derivatives in high yields and stereoselective manner. The instant invention relates to a process for the preparation of cis-hexahydroisoindoline derivative of formula II

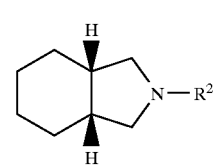

(II)

wherein $R^2$ is hydrogen, alkyl, benzyl, acyl or alkoxycarbonyl, by catalytic reduction of isoindoline derivative of formula I

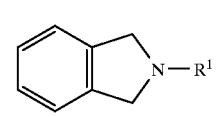

(I)

wherein $R^1$ is hydrogen, alkyl, benzyl, acyl or alkoxycarbonyl, wherein the catalytic reduction is carried out in the presence of a ruthenium, a rhodium or a palladium catalyst.

5 Claims, No Drawings

PROCESS FOR THE PREPARATION OF CIS-HEXAHYDROISOINDOLINE DERIVATIVES

BACKGROUND OF THE INVENTION

1. Field of the Invention

The present invention relates to a process for the preparation of cis-hexahydroisoindoline derivatives which are useful as starting materials for the synthesis of medicines and agricultural chemicals.

2. Prior Art

Cis-hexahydroisoindoline derivatives are usually prepared by the method reducing cis-hexahydrophthalimide or cis-$\Delta^4$-tetrahydrophthalimide with a reducing agent such as lithium aluminium hydride, sodium boron hydride, etc. This method, however, can not be industrial production since the operations thereof are tedious. In Bull. Soc. Chim. Fr. pp. 906–910, 1956, a process for the preparation of cis-hexahydroisoindoline using isoindoline as a starting material is described. However, this method leads to problems that expensive Adams platinum catalyst are used, and that the yield of product is not sufficiently quantitative.

SUMMARY OF THE INVENTION

The object of the present invention is to provide a process for the industrial preparation of cis-hexahydroisoindoline derivatives in high yields and stereoselective manner.

As a result of extensive study to solve the above problems, it has been found that a process using isoindoline derivatives as starting materials and ruthenium, rhodium or palladium as catalyst is able to attain the above object.

Thus, the present invention is to provide a process for the preparation of cis-hexahydroisoindoline derivative of formula II

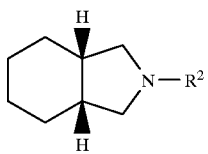

(II)

wherein $R^2$ is hydrogen, alkyl, benzyl, acyl or alkoxycarbonyl, by catalytic reduction of isoindoline derivative of formula I

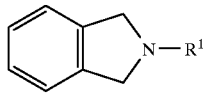

(I)

wherein $R^1$ is hydrogen, alkyl, benzyl, acyl or alkoxycarbonyl, wherein the catalytic reduction is carried out in the presence of a ruthenium, a rhodium or a palladium catalyst.

In the present invention, the substituents $R^1$ and $R^2$ have not any limitation in the carbon number thereof and can be straight-chain or branched. $R^1$ and $R^2$ defined as alkyl are, for example, methyl, ethyl, propyl, butyl, pentyl, nonyl, etc. $R^1$ and $R^2$ defined as acyl are, for example, formyl, acetyl, propionyl, butyryl, valeryl, etc. $R^1$ and $R^2$ defined as alkoxycarbonyl are, for example, methoxycarbonyl, ethoxycarbonyl, etc.

As catalyst in the present invention, a ruthenium, a rhodium or a palladium catalyst is used, and said catalyst has not any limitation except the catalyst contains at least one metal element(s) selected from the group consisting of ruthenium (Ru), rhodium (Rh) and palladium (Pd). For example, the catalyst is ruthenium-carbon, ruthenium-alumina, ruthenium oxide, ruthenium black, rhodium-carbon, rhodium-alumina, rhodium oxide, palladium-carbon, palladium-alumina, palladium-silica.alumina, palladium-barium sulfate, palladium-zeolite, palladium oxide, palladium black, etc. The amounts of the catalyst used have not any limitation, and are, for example, 0.05–10% by weight of metal(s) in the catalyst based on the starting isoindoline derivative.

In the case of carrying out in aqueous solvent the process of the present invention, the process can be performed in the pH range 1–10, preferably in from weak acidic aqueous solution to neutral aqueous solution which ranges from pH 4 to 7. In this case, the acids used may be mineral acids such as hydrochloric acid, sulfuric acid and phosphoric acid, organic acids such as acetic acid, propionic acid, benzensulfonic acid, paratoluenesulfonic acid and so on, and in particular hydrochloric acid is preferably used.

When the catalytic reduction is carried out under neutral conditions using as starting material isoindoline, N-benzylisoindoline and so on, the use of water-containing tert-butyl alcohol as solvent leads to desirable results. In the case in which the starting material are derivatives other than isoindoline and N-benzylisoindoline, to use as solvent alcohol such as methanol, ethanol, 1-propanol and 2-propanol, or water-containing solvents to which are not limited, brings to preferred results.

When isoindoline or N-benzylisoindoline are subjected to the catalytic reduction in an aqueous solvent, the amount of the acid used is important and is preferably 0.5–1.0 equivalent weight based on the starting materials. In too minor acid, as a by-product 2-methylcyclohexylmethylamine increases to result in a lowering of the yield of the aimed product, cis-hexahydroisoindoline derivatives, while in too excess acid the reaction time is elongated.

A pressure of hydrogen (hydrogen-pressure) used in the catalytic reduction of the instant process is conveniently between 5 and 50 kg/cm$^2$, most preferably between 20 and 30 kg/cm$^2$. When the hydrogen-pressure is too low, the reaction time is elongated.

Preferably, the temperature is 80–150° C., most preferably 110–140° C.

The instant process represses the formation of trans-hexahydroisoindoline derivatives and the formation of hydrogenated degradation product with a carbon-nitrogen bond, such as 2-methylcyclohexylmethylamine and so on, and economically gives cis-hexahydroisoindoline derivatives in high yields and stereoselective manner. Thus, the instant process is well suited for the industrial process.

The following examples illustrate the preparation processes of the instant invention, however, to which the instant invention is not considered to be limited.

EXAMPLE 1

In a 3-liter GL (Glass Lining) autoclave fitted with a electromagnetic stirrer are added 129 g of isoindoline, 545 g of 7.2% hydrochloric acid aqueous solution (pH 4.0) and 26 g of 5% ruthenium-carbon catalyst (50% water-containing). The reaction mixture is subjected to a hydrogen-pressure of 20 kg/cm$^2$ and a temperature of 130° C. After a 2 hour hydrogen introduction, the drop in the rate of the hydrogen-absorption is observed, at this point the introduction of hydrogen is ceased to terminate the reaction. After the termination of reaction, the catalyst is filtered out from the reacted solution. By the result of the capillary chromatographic analysis, the yield of cis-hexahydroisoindoline is 98.3%. In addition, 0.3% of trans-hexahydroisoindoline and 0.4% of 2-methylcyclohexylmethylamine is formed. After cooling the reacted solution, 240 g of 20% sodium hydroxide aqueous solution is added to neutralize, and it is extracted with toluene. After concentrating the organic phase, the residue is purified by distillation to give 128.0 g of cis-hexahydroisoindoline (yield 94.5%).

The analysis by the capillary chromatography indicates that the resulting cis-hexahydroisoindoline has the proportion of the area more than 99.0%, and that the proportions of the area of trans-hexahydroisoindoline and 2-methylcyclohexylmethylamine are 0.3% and 0.4%, respectively.

EXAMPLE 2

In a 3-liter GL autoclave fitted with a electromagnetic stirrer are added 129 g of isoindoline, 545 g of 7.2% hydrochloric acid aqueous solution (pH 4.0) and 2.6 g of 5% rhodium-carbon catalyst (50% water-containing). The reaction mixture is subjected to a hydrogen-pressure of 20 kg/cm$^2$ and a temperature of 130° C. After a 1 hour hydrogen introduction, the drop in the rate of the hydrogen-absorption is observed, at this point the introduction of hydrogen is ceased to terminate the reaction. After the termination of reaction, the catalyst is filtered out from the reacted solution. By the result of the capillary chromatographic analysis, the yield of cis-hexahydroisoindoline is 98.7%. In addition, 0.4% of trans-hexahydroisoindoline and 0.4% of 2-methylcyclohexylmethylamine is formed. After cooling the reacted solution, 240 g of 20% sodium hydroxide aqueous solution is added to neutralize, and it is extracted with toluene. After concentrating the organic phase, the residue is purified by distillation to give 130.0 g of cis-hexahydroisoindoline (yield 95.9%).

The analysis by the capillary chromatography indicates that the resulting cis-hexahydroisoindoline has the proportion of the area more than 99.0%, and that the proportions of the area of trans-hexahydroisoindoline and 2-methylcyclohexylmethylamine are 0.5% and 0.3%, respectively.

EXAMPLE 3

In a 3-liter GL autoclave fitted with a electromagnetic stirrer are added 129 g of isoindoline, 516 g of 50% water-containing tert-butyl alcohol and 26 g of 5% ruthenium-carbon catalyst (50% water-containing). The reaction mixture is subjected to a hydrogen-pressure of 30 kg/cm$^2$ and a temperature of 130° C. After a 6 hour hydrogen introduction, the drop in the rate of the hydrogen-absorption is observed, at this point the introduction of hydrogen is ceased to terminate the reaction. After the termination of reaction, the catalyst is filtered out from the reacted solution. By the result of the capillary chromatographic analysis, the yield of cis-hexahydroisoindoline is 96.0%. In addition, 0.1% of trans-hexahydroisoindoline and 3.8% of 2-methylcyclohexylmethylamine is formed. After concentrating the reacted solution, the residue is purified by distillation to give 123.2 g of cis-hexahydroisoindoline (yield 91%).

The analysis by the capillary chromatography indicates that the resulting cis-hexahydroisoindoline has the proportion of the area more than 96%, and that the proportions of the area of trans-hexahydroisoindoline and 2-methylcyclohexylmethylamine are 0.1% and 3.8%, respectively.

EXAMPLE 4

In a 3-liter GL autoclave fitted with a electromagnetic stirrer are added 226.5 g of N-benzylisoindoline, 545 g of 7.2% hydrochloric acid aqueous solution (pH 4.0) and 26 g of 5% palladium-carbon catalyst (50% water-containing). The reaction mixture is subjected to a hydrogen-pressure of 20 kg/cm$^2$ and a temperature of 130° C. After a 10 hour hydrogen introduction, the drop in the rate of the hydrogen-absorption is observed, at this point the introduction of hydrogen is ceased to terminate the reaction. After the termination of reaction, the catalyst is filtered out from the reacted solution. By the result of the capillary chromatographic analysis, the yield of cis-hexahydroisoindoline is 83.8%. In addition, 0.1% of trans-hexahydroisoindoline and 0.7% of 2-methylcyclohexylmethylamine is formed. After cooling the reacted solution, 240 g of 20% sodium hydroxide aqueous solution is added to neutralize, and it is extracted with toluene. After concentrating the organic phase, the residue is purified by distillation to give 99.7 g of cis-hexahydroisoindoline (yield 79.6%).

The analysis by the capillary chromatography indicates that the resulting cis-hexahydroisoindoline has the proportion of the area more than 99.0%, and that the proportions of the area of trans-hexahydroisoindoline and 2-methylcyclohexylmethylamine are 0.1% and 0.7%, respectively.

EXAMPLE 5

In a 3-liter GL autoclave fitted with a electromagnetic stirrer are added 265 g of N-nonylisoindoline, 735 g of 2-propanol and 26 g of 5% rhodium-carbon catalyst (50% water-containing). The reaction mixture is subjected to a hydrogen-pressure of 15 kg/cm$^2$ and a temperature of 120° C. After a 5 hour hydrogen introduction, the drop in the rate of the hydrogen-absorption is observed, at this point the introduction of hydrogen is ceased to terminate the reaction. After the termination of reaction, the catalyst is filtered out from the reacted solution. By the result of the capillary chromatographic analysis, the yield of cis-hexahydro-N-nonylisoindoline is 98.0%. In addition, 0.5% of trans-hexahydro-N-nonylisoindoline is formed.

EXAMPLE 6

In a 3-liter GL autoclave fitted with a electromagnetic stirrer are added 207 g of N-ethoxycarbonylisoindoline, 793 g of ethylalcohol and 20 g of 5% rhodium-carbon catalyst (50% water-containing). The reaction mixture is subjected to a hydrogen-pressure of 25 kg/cm$^2$ and a temperature of 130° C. After a 10 hour hydrogen introduction, the drop in the rate of the hydrogen-absorption is observed, at this point the introduction of hydrogen is ceased to terminate the reaction. After the termination of reaction, the catalyst is filtered out from the reacted solution. By the result of the capillary chromatographic analysis, the yield of cis-hexahydro-N-ethoxycarbonylisoindoline is 95.3%. In addition, 0.6% of trans-hexahydro-N-ethoxycarbonylisoindoline is formed.

EXAMPLE 7

In a 3-liter GL autoclave fitted with a electromagnetic stirrer are added 175 g of N-acetylisoindoline, 825 g of methylalcohol and 17 g of 5% ruthenium-carbon catalyst (50% water-containing). The reaction mixture is subjected to a hydrogen-pressure of 20 kg/cm² and a temperature of 110° C. After a 8 hour hydrogen introduction, the drop in the rate of the hydrogen-absorption is observed, at this point the introduction of hydrogen is ceased to terminate the reaction. After the termination of reaction, the catalyst is filtered out from the reacted solution. By the result of the capillary chromatographic analysis, the yield of cis-hexahydro-N-acetylisoindoline is 93.7%. In addition, 0.2% of trans-hexahydro-N-acetylisoindoline is formed.

What is claimed is:

1. A process for the preparation of cis-hexahydroisoindoline derivative of formula II

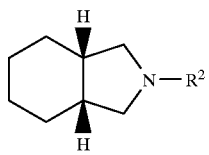
(II)

wherein $R^2$ is hydrogen, alkyl, benzyl, acyl or alkoxycarbonyl, by catalytic reduction of isoindoline derivative of formula I

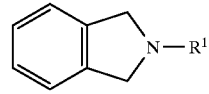
(I)

wherein $R^1$ is hydrogen, alkyl, benzyl, acyl or alkoxycarbonyl, wherein the catalytic reduction is carried out in the presence of a ruthenium, a rhodium or a palladium catalyst.

2. A process according to claim 1, wherein the catalytic reduction is carried out in an aqueous solvent of the pH range 4–7.

3. A process according to claim 1, wherein the catalytic reduction is carried out in a hydrogen-pressure of 5–50 kg/cm².

4. A process according to claim 1, wherein the catalytic reduction is carried out in a temperature of 80–150° C.

5. A process according to claim 2, wherein the catalytic reduction is carried out in a hydrogen-pressure of 5–50 kg/cm².

* * * * *